United States Patent [19]

Yim et al.

[11] Patent Number: 5,047,627
[45] Date of Patent: Sep. 10, 1991

[54] CONFIGURATION FIBER-OPTIC BLOOD GAS SENSOR BUNDLE AND METHOD OF MAKING

[75] Inventors: Jeffrey B. Yim, Woodinville; Todd W. Hubbard, Seattle; Lori D. Melkerson, Snohomish; Michael A. Sexton, Everett; Bruce M. Fieggen, Edmonds, all of Wash.

[73] Assignee: Abbott Laboratories, Abbott Park, Ill.

[21] Appl. No.: 526,185

[22] Filed: May 18, 1990

[51] Int. Cl.[5] .................. G01N 33/48; A61B 5/00
[52] U.S. Cl. .................. 250/227.23; 356/39; 356/41; 128/634
[58] Field of Search .................. 356/41, 40, 39; 128/634, 637; 250/227.23, 226

[56] References Cited

U.S. PATENT DOCUMENTS

| | | | |
|---|---|---|---|
| 4,114,604 | 9/1978 | Shaw et al. | 128/2 L |
| 4,295,470 | 10/1981 | Shaw et al. | 128/634 |
| 4,476,870 | 10/1984 | Peterson et al. | 128/634 |
| 4,600,310 | 7/1986 | Cramp et al. | 356/432 |
| 4,718,423 | 1/1988 | Willis et al. | 128/634 |
| 4,752,115 | 6/1988 | Murray, Jr. et al. | 350/96.29 |
| 4,760,250 | 7/1988 | Loeppert | 250/227.23 |
| 4,785,814 | 11/1988 | Kane | 128/634 |
| 4,803,049 | 2/1989 | Hirschfeld et al. | 422/58 |
| 4,810,655 | 3/1989 | Khalil et al. | 436/138 |
| 4,830,013 | 5/1989 | Maxwell | 128/637 |
| 4,919,891 | 4/1990 | Yafuso et al. | 422/58 |
| 4,951,669 | 8/1990 | Maxwell et al. | 128/634 |
| 4,954,318 | 9/1990 | Yafuso et al. | 356/39 |

FOREIGN PATENT DOCUMENTS

| | | | |
|---|---|---|---|
| 0336985 | 10/1989 | European Pat. Off. | 128/634 |
| 0352610 | 1/1990 | European Pat. Off. | 128/634 |

OTHER PUBLICATIONS

Scheggi et al., "Optical Fiber Sensors in Modern Clinical Care," FPN, Cover Story Tutorial, Mar. 1990, pp. 17-23.
Gehrich et al., "Optical Fluorescence and Its Application to an Intranscular Blood Gas Monitoring System" IEEE, vol. BME-33, No. 2, 2/86, pp. 117-132.

Primary Examiner—David C. Nelms
Assistant Examiner—Michael Messinger
Attorney, Agent, or Firm—Christensen, O'Connor, Johnson & Kindness

[57] ABSTRACT

A bundle of fiber-optic sensors that resist breakage, for use in measuring pH, $CO_2$, and $O_2$ concentration, and a method of making the same. Three otpical fibers are enclosed in a common polyimide sheath and extend parallel to one another toward a distal end of the sensor, where they are bonded together in a mutually supportive array. At the distal end of one of these optical fibers is disposed a pellet comprising a $CO_2$ analyte indicator molecule codissolved within a polymer matrix. A thin reflective surface of gold foil is provided on the pellet such that incident light transmitted through the optical fiber and polymer matrix is reflected back into the optical fiber. The $CO_2$ polymer matrix absorbs light of a given wavelength to an extent dependent upon the level of $CO_2$ present. Similarly, on the distal end of a second optical fiber is disposed a pH pellet comprising a pH analyte indicator matrix with a thin reflective gold foil attached for reflecting light that has passed through the pH analyte indicator matrix back into the optical fiber. The pH analyte indicator matrix absorbs light of a given wavelenth to an extent dependent upon the hydrogen ion concentration (pH level) of a surrounding fluid. The third optical fiber is used for measuring oxygen concentration. An $O_2$ indicator matrix covers the distal ends of at least two of the three optical fibers; however, at least a portion of the pH optical fiber and the pH pellet are free of the $O_2$ indicator matrix, which is hydrophobic. The oxygen indicator matrix phosphoresces for an interval of time that decreases in proportion to the surrounding oxygen gas concentration. The phosphorescent and reflected light signals are transmitted to light detectors through the optical fibers for comparison to reference signals, so that the analyte concentrations can be determined.

22 Claims, 3 Drawing Sheets

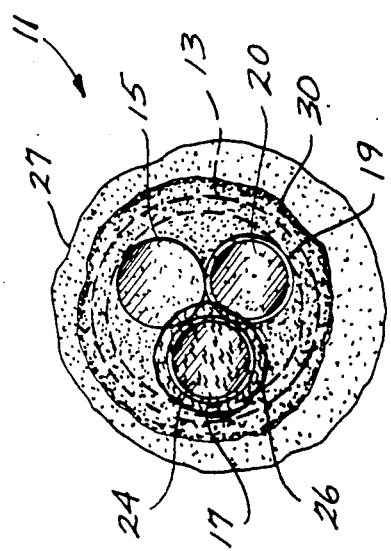
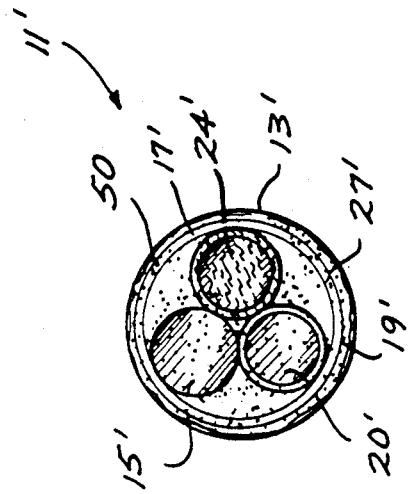
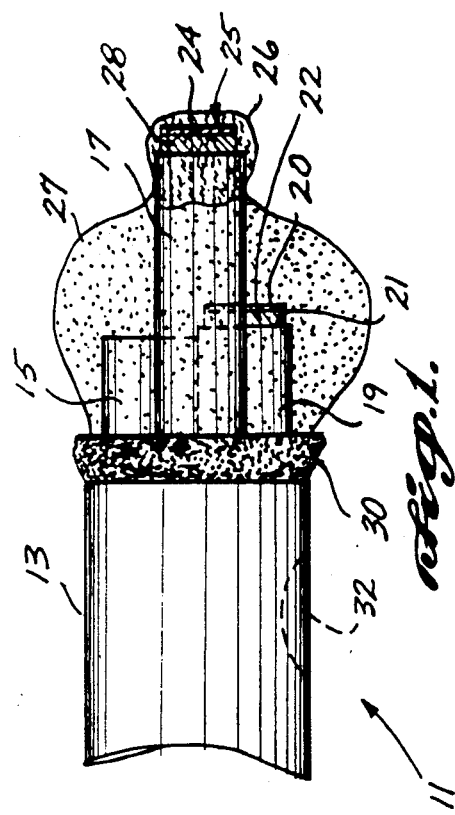
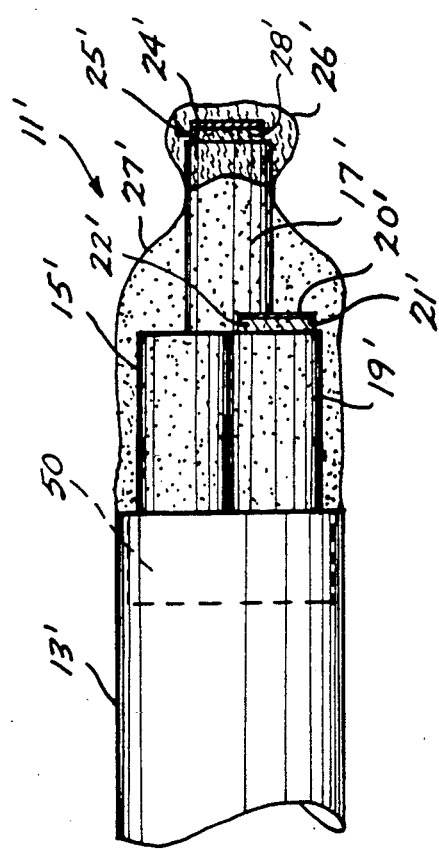

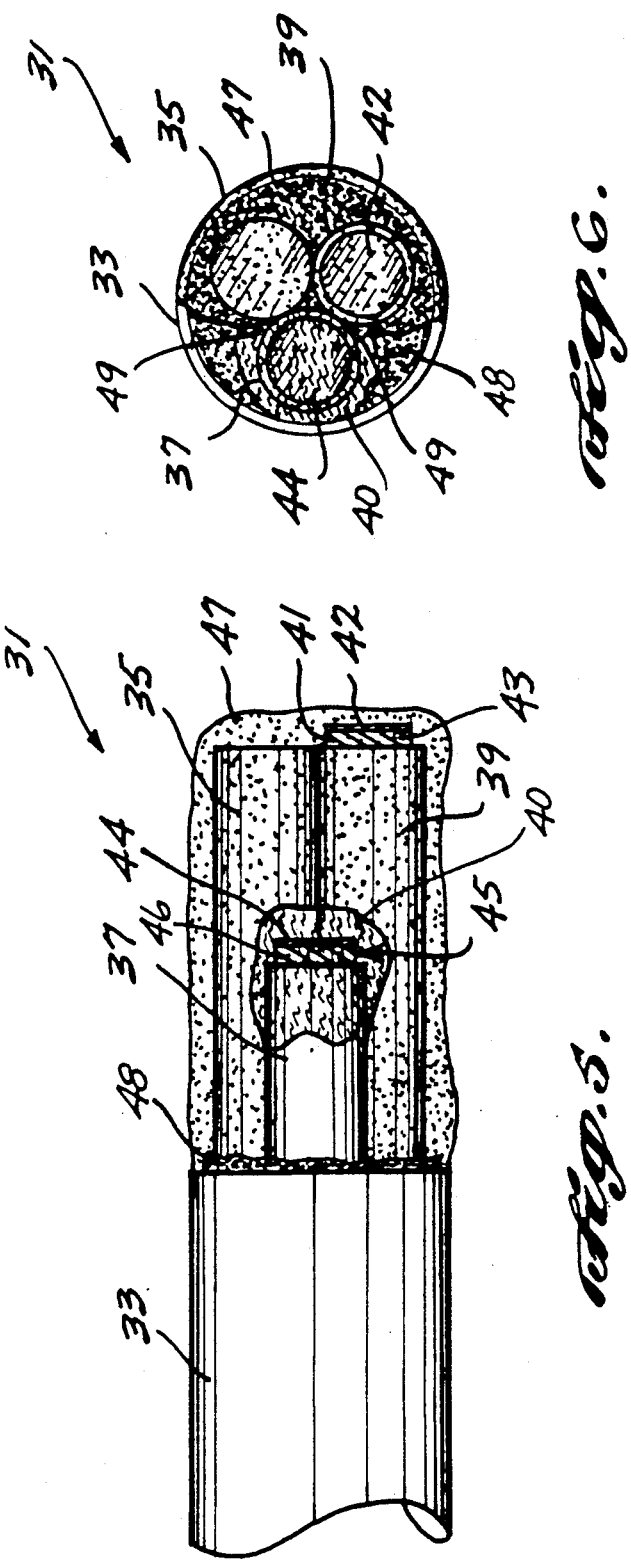

CONFIGURATION FIBER-OPTIC BLOOD GAS SENSOR BUNDLE AND METHOD OF MAKING

TECHNICAL AREA

This invention relates to fiber-optic sensors suitable for monitoring physiological pH and blood gas concentrations.

BACKGROUND OF THE INVENTION

In recent years, fiber-optic chemical sensors have been developed to detect the presence and monitor the concentration of various analytes such as oxygen and carbon dioxide gas, as well as pH. Such sensors are based on the recognized phenomenon that the absorbance and, in some cases, the luminescence, phosphorescence, or fluorescence of certain indicator molecules are perturbed in the presence of specific analyte molecules. The perturbation of the light emission properties and/or absorbance profile of an indicator molecule can be detected by monitoring radiation that is absorbed, reflected, or emitted by it when illuminated in the presence of a specific analyte.

Fiber-optic probes that position an analyte sensitive indicator molecule in a light path optically monitor the effect of the analyte on the indicator molecule. Typically, for monitoring carbon dioxide or pH level, the optical fiber transmits electromagnetic radiation from a light source to the indicator molecule, and the level of absorbance as measured by the light reflected from the vicinity of the indicator molecule gives an indication of the gaseous analyte or hydrogen ion concentration. Alternatively, for monitoring other types of gases, such as $O_2$, the optical fiber transmits electromagnetic radiation to the indicator molecule, exciting it to emit light, e.g., to phosphoresce. The duration of phosphorescence by the indicator molecule serves as an indication of the concentration of the gas in the surrounding fluid. These indicator molecules are typically disposed in a sealed chamber at the distal end of the optical fiber, with the chamber walls being permeable to the analyte, but not permeable to liquids.

One problem with known sensing systems of the type described is that the optical fiber and sealed chamber attached to the end of the probe are prone to physical damage. The optical fibers and attached sensors are delicate because they are situated as an external appendage located at the end of a catheter used to invasively insert the probe and extend distally beyond it. Any mishandling of the catheter can easily result in damage to the delicate chamber or optical fiber.

Another problem with the systems described above is that the probe can encourage the formation of blood clots, or thrombi. Prior art multifiber sensors provide interfiber crevices, which encourage thrombi formation, even in the presence of an anti-coagulant heparin solution.

A sensor disposed at the distal end of an optical fiber is sometimes subject to a phenomenon referred to as "wall effect" wherein the sensor impinges on the inner wall of an artery or vein and monitors the $O_2$ concentration or other parameter at the vessel wall rather than measuring the parameter in the blood circulating through the vessel. A significant gradient can exist between the measured level of the parameter in free flowing blood at a position close to the center of the vessel and at the vessel wall. A sensor that is relatively small in diameter and is mounted at a distal-most end of an optical fiber is more likely to experience an error due to wall effect than one that comprises part of a multi-sensor bundle of larger overall diameter, because of the more limited surface area of the smaller sensor and its inherent propensity to lie closer to the vessel wall.

SUMMARY OF THE INVENTION

In accordance with the present invention, a fiber-optic sensor suitable for monitoring physiological analyte concentrations includes a first, a second, and a third optical fiber, each having a longitudinal axis corresponding to the direction that light propagates through the optical fiber. The optical fibers are arranged so that their longitudinal axes are substantially parallel.

A first indicator matrix containing a first indicator molecule is disposed adjacent the distal end of the first optical fiber. Similarly, adjacent to the distal end of the second and third optical fibers are respectively disposed a second indicator matrix containing a second analyte sensitive indicator molecule, and a third indicator matrix containing a third indicator molecule. Each of the indicator molecules exhibit signals corresponding to the three analyte concentrations in response to light of three wavelengths. The optical fibers are arranged and bonded together in a mutually supportive array that substantially reduces the likelihood of any of the three optical fibers breaking during use.

Further, disposed adjacent the first and second indicator matrices are first and second light reflectance materials. The light reflectance materials reflect light signals back into the optical fibers after the light signals are transmitted through and partially absorbed by the indicator matrices.

The distal ends of the optical fibers are preferably aligned in a triangular array. A protective sheath surrounds at least a portion of the three optical fibers, but not their distal ends. At least one of the indicator matrices is generally pellet shaped and is attached to a substantially planar face of a corresponding one of the optical fibers. The distal ends of the optical fibers are overcoated such that the blood gas sensor has a hydrodynamic shape.

In one embodiment, at least two of the optical fibers extend distally of the other optical fiber. Furthermore, in that embodiment, those two optical fibers are overcoated with a hydrophobic material and the other optical fiber is overcoated with a hydrophilic material.

Another aspect of the present invention is a method for making the sensor, including the steps of assembling the particular components of the above-described sensor.

BRIEF DESCRIPTION OF THE DRAWINGS

The advantages of this invention will become more readily apparent as the same becomes better understood by reference to the following detailed description when taken in conjunction with the accompanying drawings wherein:

FIG. 1 is a schematic longitudinal view of the fiber-optic probe sensor in a first preferred configuration;

FIG. 2 is an end view of FIG. 1;

FIG. 3 is a schematic longitudinal view of the fiber-optic sensor in a second preferred configuration;

FIG. 4 is an end view of FIG. 3;

FIG. 5 is a schematic longitudinal view of the fiber-optic sensor in a third preferred configuration;

FIG. 6 is an end view of FIG. 5; and

DETAILED DESCRIPTION OF THE PREFERRED EMBODIMENTS

Geometrical Configurations of Sensor

Figure 7:
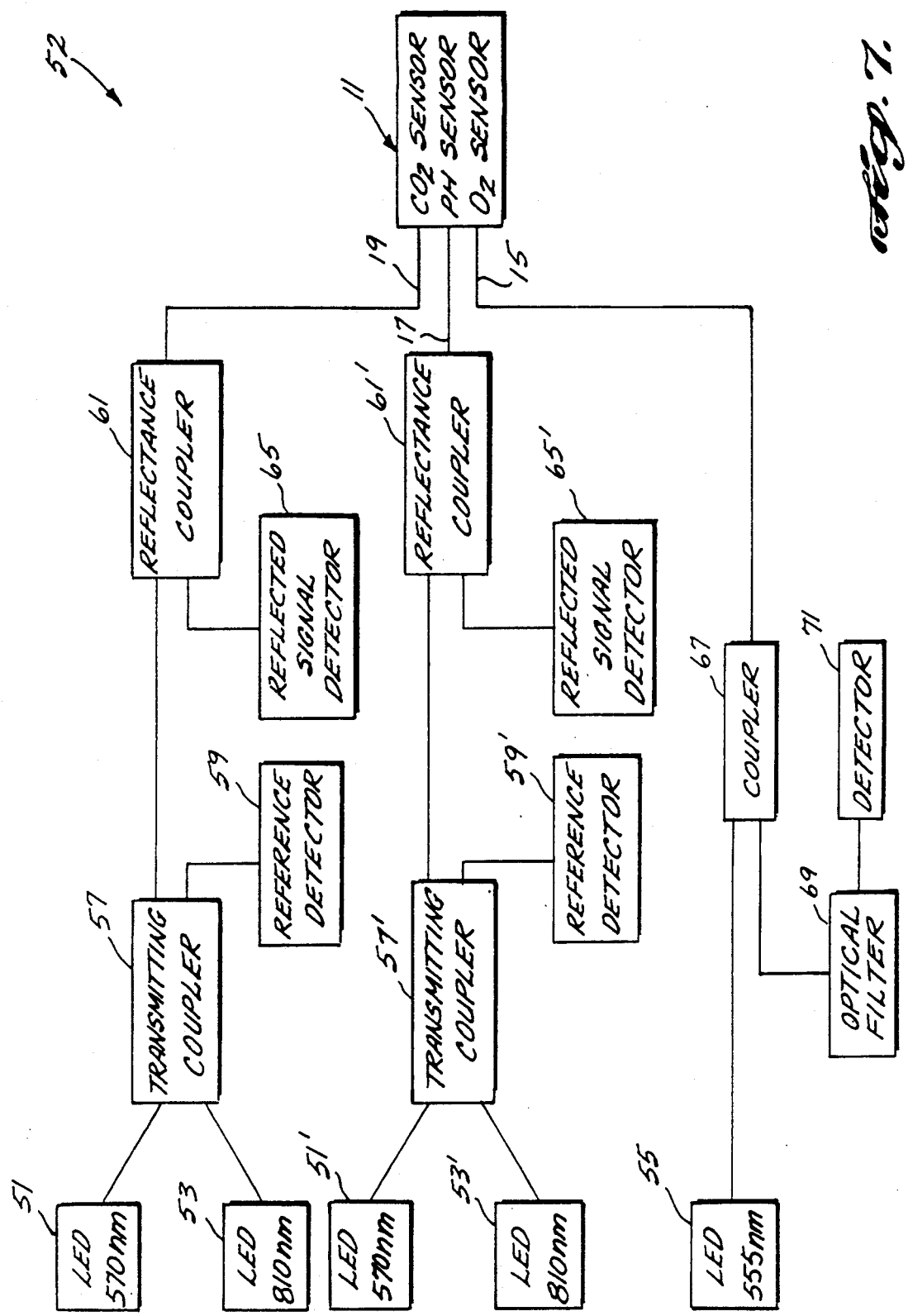
FIG. 7 is a block diagram of a system using the present fiber-optic sensor to measure $CO_2$, $O_2$, and pH of a fluid.

A first preferred embodiment of the fiber-optic sensor of this invention is shown in FIGS. 1 and 2, generally at reference numeral 11. Fiber-optic sensor 11 comprises three individual optical fibers 15, 17, and 19 encased in a polyimide sheath 13. More specifically, the three optical fibers are arranged such that the longitudinal axes (the axes generally corresponding to the path of a light signal propagating therein) of the optical fibers are parallel and are arranged in an equilateral triangular array. Optical fiber 15 conveys light signals used to sense oxygen ($O_2$) concentration, optical fiber 17 is used to convey light signals for sensing hydrogen ion concentration (pH), and optical fiber 19 is used for conveying light signals for sensing carbon dioxide ($CO_2$) concentration. In this first preferred embodiment, $O_2$ optical fiber 15 and $CO_2$ optical fiber 19 both extend about 500 micrometers beyond polyimide sheath 13, but the distal end of pH optical fiber 17 extends beyond the distal ends of $O_2$ optical fiber 15 and $CO_2$ optical fiber 19 by about 250 micrometers. However, these dimensions can vary significantly.

The distal ends of all three optical fibers are cleaved perpendicular to their longitudinal axes, and each distal end comprises a substantially planar, circular surface. Disposed upon the circular surface of $CO_2$ optical fiber 19 is a substantially cylindrical $CO_2$ pellet 21 (i.e., a sensor for $CO_2$ in pellet form) having a diameter approximately equal to that of optical fiber 19. $CO_2$ pellet 21 includes a $CO_2$ analyte sensitive matrix material 22 and a thin film of reflective material 20, preferably comprising gold foil. The thin film of reflective material 20 is incorporated into the distal circular surface of $CO_2$ pellet 21, is substantially concentric with the cylindrical surface of the $CO_2$ pellet 21, and is situated such that a light signal propagated through $CO_2$ optical fiber 19 and $CO_2$ pellet 21 is reflected by reflective material 20 back into $CO_2$ optical fiber 19. The $CO_2$ pellet and the circular face of $CO_2$ optical fiber 19 are preferably perpendicular to the longitudinal axis of optical fiber 19 in order to most efficiently reflect transmitted incident light conveyed through optical fiber 19 back into the optical fiber. $CO_2$ pellet 21 preferably has a longitudinal thickness on the order of 25 micrometers.

Similarly, a cylindrical pH pellet 25 (i.e., a sensor for pH in pellet form) is attached to the distal end of pH optical fiber 17. The pH pellet 25 is preferably sized so as to substantially cover the entire circular surface of the distal end of pH optical fiber 17, and includes a pH analyte sensitive material 28 and a thin film of reflective material 24, preferably comprising gold foil. The thin film of reflective material 24 is incorporated onto the distal circular surface of pH pellet 25, is substantially concentric with the surface of pH pellet 25, and is situated such that a light signal propagated down pH optical fiber 17 and through pH pellet 25 is reflected by reflective material 24 back into pH optical fiber 17. The thickness of pH pellet 25 is preferably on the order of 40 micrometers.

Still referring to FIGS. 1 and 2, it can be seen that an $O_2$ indicator matrix 27 encapsulates the entire distal ends of $O_2$ optical fiber 15 and $CO_2$ optical fiber 19, $CO_2$ pellet 21, and a substantial portion of pH optical fiber 17 that extends beyond polyimide sheath 13. The $O_2$ indicator matrix is hydrophobic, yet allows gas molecules to pass freely. Hydrogen ions are blocked by $O_2$ indicator matrix 27 because it is impermeable to aqueous solutions in which the hydrogen is ionized. However, pH optical fiber 17 extends distally beyond $O_2$ indicator matrix 27 such that the distal end of pH optical fiber 17 is completely free of $O_2$ indicator matrix 27. Further, an overcoat of a pH indicator matrix material 26 that is more fully described below, is applied such that the free distal end of pH optical fiber 17 is also hydrodynamically encapsulated. Since pH indicator matrix material 26 is hydrophilic, hydrogen ions pass freely through it.

The $O_2$ indicator matrix binds all three optical fibers into a rugged, mutually supportive assembly that resists damage and breakage of any single optical fiber due to mishandling. An epoxy seal 30 surrounds the base of $O_2$ indicator matrix 27, sealing the distal end of polyimide sheath 13 and further bonding the assembly of optical fibers into an integral probe. This epoxy seal is either flowed into the end of polyimide sheath 13 or is injected through an optional orifice 32, which is disposed in the polyimide sheath adjacent to its distal end. The relatively larger diameter of sensor 11 compared to prior art designs or to an individual sensor also minimizes wall effects that might otherwise create errors in measuring $O_2$ concentration in the blood.

A second embodiment of the fiber optic sensor shown in FIGS. 3 and 4, reference numeral 11', is very similar to sensor 11 of FIGS. 1 and 2. Accordingly, the same reference numerals are used for elements of sensor 11' that provide a similar form and function, with a "prime" notation added to distinguish elements of the second embodiment from the first. As in the previous configuration for sensor 11, the longitudinal axes of an $O_2$ optical fiber 15', a pH optical fiber 17', and a $CO_2$ optical fiber 19' are parallel and arranged in an equilateral triangular array, with the three optical fibers all mutually adjacent to one another. The distal end of each optical fiber extends beyond a polyimide sheath 13', which encases much of the remaining proximal length of each optical fiber. However, in sensor 11', epoxy seal 30 is not applied externally to the sensor. Instead, a polyimide sleeve 50 holds the optical fibers in the triangular array, and an epoxy adhesive (not shown) is applied to the distal end of polyimide sheath 13' during construction of the sensor to seal the distal end of the polyimide sheath before an $O_2$ indicator matrix 27' is formed around the optical fibers. Polyimide sleeve 50 is generally cylindrical and slightly smaller in diameter than polyimide sheath 13'. The polyimide sleeve is forced inside the distal end of polyimide sheath 13' so that the distal ends of the two polyimide structures are approximately aligned.

A $CO_2$ pellet 21', which is identical in form and function to $CO_2$ pellet 21 of the previous embodiment, is attached to $CO_2$ optical fiber 19'. Similarly, a pH pellet 25', substantially identical in form and function to pH pellet 25 of the previous embodiment, is attached to the distal end of pH optical fiber 17'. Still referring to FIGS. 3 and 4, it can be seen that $O_2$ indicator matrix 27' encapsulates the entire distal portion of $O_2$ optical fiber 15', $CO_2$ optical fiber 19', and $CO_2$ pellet 21', and a substantial portion of pH optical fiber 17' that extends beyond polyimide sheath 13.

The length of $CO_2$ optical fiber 19', pH optical fiber 17', and $O_2$ optical fiber 15' extending from polyimide sheath 13' is substantially the same as in sensor 11 (FIGS. 1 and 2). Further, an overcoat of pH indicator matrix material 26' completely encloses the free distal end of pH optical fiber 17'.

A third embodiment of the fiber-optic sensor is shown in FIGS. 5 and 6, generally at reference numeral 31. Sensor 31 comprises three individual optical fibers 35, 37, and 39 enclosed in a polyimide sheath 33 over much of their length. More specifically, the three optical fibers are arranged mutually adjacent each other, such that their longitudinal axes are parallel, forming an equilateral triangular array. Optical fiber 35 is used in connection with sensing $O_2$ concentration; optical fiber 39 is used in connection with sensing $CO_2$ concentration; and optical fiber 37 is used for sensing pH. Moreover, the distal end of pH optical fiber 37 extends a shorter distance from polyimide sheath 33 than $O_2$ optical fiber 35 and $CO_2$ optical fiber 39, and is thus recessed from the distal ends of the other two optical fibers.

In this third embodiment, $O_2$ optical fiber 35 and $CO_2$ optical fiber 39 preferably extend beyond polyimide sheath 33 by approximately 500 micrometers. However, it will be appreciated that this extension may range, for example, from 500–750 micrometers. The distal end of pH optical fiber 37 preferably extends beyond polyimide sheath 33 by approximately 300–500 micrometers (but less than the extension of the $CO_2$ and $O_2$ optical fibers).

The distal ends of all three optical fibers are cleaved perpendicular to their longitudinal axes such that each distal end comprises a generally planar, circular surface. Disposed upon the circular surface of $CO_2$ optical fiber 39 is a substantially cylindrical $CO_2$ pellet 41 having a diameter approximately equal to that of optical fiber 39. $CO_2$ pellet 41 is generally equivalent to the earlier noted $CO_2$ pellet 21, and includes a thin layer of reflective material 42 attached to a $CO_2$ analyte sensitive material 43.

Similarly, a pH pellet 45 is attached to the distal end of pH optical fiber 37 and is preferably sized so as to substantially cover its entire circular surface. Thus, pH pellet 45 includes a thin layer of reflective material 44 attached to a pH sensitive material 46 and is substantially similar to the earlier described pH pellet 25. The thickness of pH pellet 45 is preferably on the order of 50 micrometers.

Still referring to FIGS. 5 and 6, it can be seen that an $O_2$ indicator matrix 47 (same composition as $O_2$ indicator matrix 27) encapsulates the entire distal portion of $O_2$ optical fiber 35 and $CO_2$ optical fiber 39, and $CO_2$ pellet 41. However, the distal end of pH optical fiber 37 is not encapsulated by $O_2$ indicator matrix 47. Thus, the arrangement results in pH optical fiber 37 being recessed from the distal ends of encapsulated $O_2$ optical fiber 35 and $CO_2$ optical fiber 39, but free of $O_2$ indicator matrix 47. Due to crevices 49 that exist between pH optical fiber 37 and $O_2$ indicator matrix 47, sensor 31 is more subject to formation of thrombi than the other two embodiments.

Chemical Composition and Fabrication of Indicator Matrixes

The chemical composition of $CO_2$ pellets 21 and 41 and pH pellets 25 and 45 is comprised basically of an appropriate analyte indicator molecule codissolved within a polymer matrix. (Note that in the following discussion, a reference to $CO_2$ pellets 21 also applies to $CO_2$ pellets 21' and a reference to pH pellets 25 also applies to pH pellets 25'.) Specifically, $CO_2$ pellets 21 and 41 comprise sodium bicarbonate, a $CO_2$ analyte indicator molecule such as phenol red, and the polymer matrix, all coupled with the thin film of gold foil reflective material. Similarly, pH pellets 25 and 45 comprise the pH analyte indicator molecule, phenol red, and the polymer matrix, all coupled with the thin film of gold foil reflective material.

The base polymer matrix used as a carrier for the analyte indicator molecules is identical for the pH and $CO_2$ pellets; the choice of materials for the polymer matrix is influenced by the need to simultaneously satisfy many requirements. For pH pellets 25 and 45, the polymer matrix must immobilize the indicator molecule in the light path defined by the axial core of the optical fibers. Otherwise, signal drift can result due to leakage of indicator molecules from the polymer matrix, especially water soluble molecules such as phenol red. The water soluble indicator molecules must therefore be covalently bonded to a component of the polymer matrix. However, in $CO_2$ pellets 21 and 41, the indicator molecules need not be covalently bonded, since $O_2$ indicator matrix 27 (more fully described below), which encapsulates $CO_2$ pellets 21 and 41, in part comprises a hydrophobic silicone material. Thus, $CO_2$ pellets 21 and 41 are not exposed to aqueous liquids, and the phenol red does not leak from the polymer matrix.

Further, the polymer matrix must also permit free bidirectional movement of the subject analyte, i.e., the polymer matrix must be permeable to the $CO_2$ and pH analyte. For physiological applications in which the analyte is dissolved or dispersed in aqueous solutions, the polymer matrix must be hydrophilic as well as porous to the analyte substance. However, the hydrophilicity of the polymer matrix must be regulated to prevent undue swelling, with attendant risk of dissociation from the fiber end when the optical fiber is immersed in aqueous solutions such as blood, lymph fluid, extracellular fluid, and/or serum. Furthermore, swelling in an aqueous solution should not cause differential movement of the polymer matrix, vis-a-vis the light transmitting optical fiber, particularly during use of the sensor.

The polymer matrix should have a refractive index that is sufficiently matched to that of the optical fiber to minimize light scattering effects, such as Fresnel losses, and must be capable of sustaining its attachment onto the end of the optical fiber. Also, the polymer matrix should not shrink or crack upon drying. Finally, the polymer matrix should retain its rigidity and strength during use, e.g., by having sufficient wet mechanical strength to maintain its integrity while being manipulated through blood vessels.

A material that satisfies the foregoing requirements for the polymer matrix is made by copolymerizing a mixture of about 94 mole percent (mole %) methylmethacrylate (MMA) and about 6 mole % methacrylamidopropyltrimethylammonium chloride (MAPTAC) as disclosed in U.S. Pat. No. 4,434,249. Polymethyl methacrylate-based material is an especially appropriate matrix component because it provides a good refractive index match when used with plastic optical fibers having methacrylate cores. This copolymer is highly permeable to water and small ions, especially anions, while meeting all the other requirements mentioned above. Methylmethacrylate can alternatively be copolymerized or alloyed with other ionogenous or neutral monomers such as hydroxymethyl methacrylate, N-vinylpyrrolidone, or acrylic acid, to confer analyte permeability to the resulting polymer matrix. N-vinylpyrrolidone/p-aminostyrene copolymer 60:40 to 80:20 wt./wt is another suitable resin material. Suitable solvents for these resins are known to include alcohols, N,N-dimethylacetamide (DMAC), N,N-dimethylformamide, methyl ethyl ketone, tetrahydrofuran, esters, and aromatic and chlorinated hydrocarbons.

The indicator molecule is selected to respond optically to the presence of the targeted analyte (e.g., $CO_2$ or pH) when immobilized in the polymer matrix. For continuous monitoring of analyte concentration, the reaction or response between the indicator molecule and the analyte should be reversible as well as sensitive and specific. Suitable analyte sensitive indicator molecules are generally well known in the art for other analytes of interest besides pH and $CO_2$.

As noted earlier, in pH pellets 25 and 45, covalent bonding functions to immobilize water-soluble indicator molecules within the polymer matrix but otherwise must not significantly adversely impact upon the sensitivity, specificity, and reversibility of its optical response to the targeted analyte. Thus, analyte sensitive sites on the indicator molecule must not be eliminated or sterically hindered upon covalent binding to the resin. The indicator molecule should therefore be uniformly bound to the resin in a site-specific manner that preserves the optical responsiveness of the indicator to the analyte, using a reaction protocol that prevents or substantially eliminates heterogeneous reaction products.

For this purpose, aminoarylalkylamines are preferably employed to covalently link the indicator molecule to a polymer, which is thereafter admixed in solvent with other matrix components to form an emulsion or solution. Suitable aminoarylalkylamines have the formula:

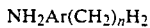

$NH_2Ar(CH_2)_nH_2$ wherein Ar is nonsubstituted or preferably, substituted phenyl, and n is an integer. Preferably, n equals 2 or 3, in order to avoid hydrocarbon characteristics associated with longer alkyl chains. The aminoarylalkylamine is preferably para-substituted. Exemplary aminoarylalkylamines for practicing the invention are 4-(aminophenyl)-ethylamine and 4-(aminophenyl)-(propellamine).

Heterogeneous reaction products are prevented by specifically attaching the alkylamino moiety to the polymer before reacting the arylamino moiety with the indicator molecule. The aminoarylalkylamine is first attached to a polymeric resin component, such as MMA/MAPTAC, by reaction in ethanol at 70° C. with triethylamine as a catalyst. The free arylamino group is then reacted with the indicator molecule of choice, for example, by using a diazotization for coupling with indicator molecules such as phenol red having strong electron releasing groups or by formation of an amidyl linkage with carboxylic acid bearing indicator molecules. The available diazonium binding sites should be saturated with an excess of indicator molecules during this second reaction step, in order to provide a polymeric resin component containing a concentrated amount of indicator molecule.

However, as noted earlier, the $CO_2$ indicator molecule need not be covalently bonded to the polymer matrix. In the exemplary formation of $CO_2$ analyte sensitive material comprising $CO_2$ pellets 21 and 41 without covalent bonding, the following protocol may be followed. One gram of solid PEG 600k is dissolved in 19 grams of 2-methoxyethanol (5% wt./wt.) and stirred or sonicated until homogeneous. The solution of MMA/MAPTAC (94:6) is prepared by dissolving one gram of solid MMA/MAPTAC in 6.7 grams of 2-methoxyethanol (13% wt./wt.) and stirring until homogeneous. Next, 3.07 grams of the 13% MMA/MAPTAC solution is mixed with 2 grams of the 5% PEG 600k solution. The ratio of the solid MMA/MAPTAC to solid PEG 600k is 80% to 20%. The admixed solution may be sonicated for up to five minutes to insure a homogeneous solution. To this mixed solution, 0.005 grams of phenol red is added and stirred until homogeneous. Finally, 200 microliters of 0.875 Molar bicarbonate solution is added to the phenol red and the MMA/MAPTAC solution to form the $CO_2$ polymer matrix solution used to form $CO_2$ analyte sensitive matrix material 22. In an alternative approach, the $CO_2$ analyte indicator molecule may be covalently bonded with the MMA/MAPTAC polymer using the aminoarylalkylamines noted earlier to form the $CO_2$ polymer matrix solution.

Regardless of the particular polymer matrix solution used, chemically bonded or admixed, the next step in the manufacture of $CO_2$ pellets 21 and 41 consists of applying the polymer matrix solution to the gold foil reflective material. To illustrate, gold foil is available in 1-inch by 12-inch strips, shipped on a plastic roll. The gold foil is prepared by placing the foil between two clean glass slides, and cutting away a 1-centimeter by 2½-centimeter strip. The strip is cut in half once again, such that there are two 1-centimeter by 1.25-centimeter pieces. Each foil piece is measured for thickness using, e.g. a Mitutoyo Digital Micrometer, and checked for uniformity. Each piece of foil is placed in a scintillation vial and 1 ml of concentrated HCl is added. The foil is allowed to soak in the concentrated HCl for at least two hours, but preferably for 8-12 hours to remove any residues on the gold foil surface. The gold foil is removed from the vial of concentrated HCl and rinsed with copious amounts of distilled water, at least three times on each side. Then, the gold foil is placed on a glass slide and any moisture is removed from the gold surface with blotting paper. Finally, the shininess of the gold foil is examined for impurities. (If spots/impurities appear on the gold foil, it is replaced in the concentrated HCl, and the cleaning process is repeated.)

Using adhesive tape, the gold foil is attached to a glass slide. Preferably, the gold foil is taped down such that the surface of the foil is flat (by stretching the gold foil after it is taped down), and a 1-centimeter by 1-centimeter area of the gold foil is exposed. The tape is next masked to prevent the dye solvents from dissolving the tape mount and, hence, destroying the film prep. A bead of UV-curable adhesive, (e.g., NOA-81 supplied by Norland Products, Inc., New Brunswick, N.J.) is placed along the tape on both sides of the gold foil. Using a No. 2 paint brush, the adhesive is brought over the tape and right up to, but not onto the surface of the gold foil. Should the NOA-81 adhesive leach onto the gold foil surface, the adhesive is cured under a 365 nm UV lamp, peeled away, and reapplied. Once the NOA-81 has been brought to the edge of the gold foil on both sides, such that it completely covers the tape, but does not extend onto the gold foil surface, the NOA-81 is cured by placing it under a 365 nm UV lamp for about five minutes.

A leveling plate is placed on top of a Corning hot plate/stirrer, which is set to provide a temperature of about 45°–55° C. A two-way level is used to adjust the height of the screws on the leveling plate until the plate is level. The glass slide containing the gold foil mount is placed onto the leveling plate and allowed to achieve temperature equilibrium. The solution of the polymer matrix and the indicator molecule as produced by the process described earlier are placed into an oven and allowed to reach 45° C. A 50 microliter aliquot of the polymer matrix (10% wt./wt.) solution is placed onto the surface of the gold foil with a micropipette. The micropipette tip can be used to brush the dye over the entire surface of the gold. However, care should be taken such that the dye is not applied beyond the foil edge. Should this happen, the sample is removed and the application repeated with a new foil mount. Any bubbles in the film surface should be removed by blowing air through the micropipette tip.

The measured amounts of dye given for the film preps here are based on an exposed gold area of one square centimeter. For mounted foils having exposed surface areas other than one square centimeter, the exposed area is multiplied by the amount of dye given for one square centimeter, and that amount of dye is applied to the foil surface.

Next, a 7-centimeter drying tube is placed over the sample. The leveling plate and the gold foil are left undisturbed, allowing approximately two hours for the film to dry. After the drying process is complete, the gold foil must be cut from the glass slide and measured for thickness to assure uniformity. Using adhesive tape, all four sides of the gold film should next be attached to the counter, allowing the tape to cover about 1 millimeter of the film on each side. Using the end of a bull-nosed tweezers, the adhesive tape is secured to the film by compressing the tape down onto the film surface, being careful not to scrape the film surface. Any excess tape is trimmed, so that the film mount is square. The film mount is removed from the counter and inverted onto a glass slide. Thin strips of adhesive tape are placed around the underside of the film, such that the tape extends over the gold surface, but not beyond the tape on the film side of the sample. Again, the end of the bull-nosed tweezers is used to compress the tape securely against the foil. The film mount is centered onto the micro punch XY plate, dye side up, and taped to the XY plate such that the film lies flat and there are no folds in the adhesive tape. The underside of the sample is checked to be sure that the gold foil is clean prior to securing the XY plate to a micro punch (e.g., Model #001, Abbott Reasearch, Inc., Bothell, Wash.). The $CO_2$ pellets 21 that are punched from the gold foil are then used in the construction of the analyte probe, by attaching a pellet comprising $CO_2$ analyte sensitive material 22 to the distal end of the optical fiber.

The pH pellets 25 and 45 are constructed in a similar manner. A pH indicator molecule, such as phenol red, is codissolved with the same polymer matrix as was used to make the $CO_2$ pellets 21 and 41. Because phenol red is water soluble and pH pellets 25 and 45 are completely exposed to aqueous fluids during use, it must be covalently bonded to the polymer matrix. Thus, as stated earlier, an aminoarylalkylamine is used to effectuate the covalent bonding. In one embodiment, 4-(amino phenol)-ethylamine (APE) is attached to the MMA/MAP-TAC polymer. Initially, the APE is purified as the dihydrochloride by taking 4 grams of APE (Aldrich Chemical Company, Inc., Milwaukee, Wis.) in 8 milliliters of concentrated hydrochloric acid at 0° C. and recrystallizing the dihydrochloride from water ethanol (100 milliliters of 95:5 water-ethanol). Next, 2 milliliters of 10% MMA/MAPTAC solution is azeotroped with anhydrous ethanol (three aliquots of 50 milliliters each) and redissolved in 25 milliliters anhydrous ethanol. Subsequently, 0.38 grams of the APE-dihydrochloride and 1 milliliter of freshly distilled triethylamine as a catalyst are added, and the solution is stirred in an oven at 55° C. for 48 hours. The solvent and excess triethylamine are removed in a rotary evaporator.

The MMA/MAPTAC polymer with the APE attached is then used as the medium for carrying the phenol red indicator molecule. The coupling of the phenol red to the APE/MMA/MAPTAC is accomplished as follows. The APE/MMA/MAPTAC reaction product is dissolved in 20 milliliters of denatured ethanol at 0° C. and to that solution is added 3 milliliters of concentrated HCl and 3 milliliters of water. Next, a solution of 0.3 grams of $NaNO_2$ in 2 milliliters of water is added and the solution is stirred at 0° C. for three hours. This solution is then added to 2.4 grams of phenol red and 2.5 grams of $KHCO_3$ in 30 milliliters of water and 30 milliliters of denatured ethyl alcohol, while stirring at 0° C. It is important when coupling the diazotized APE polymer to phenol red to maintain the solution pH at about 8.5 using $KHCO_3$ and to use excess phenol red in order to saturate all diazotized sites and prevent diazonium hydroxide/phenol formation. The resulting solution is stirred overnight at 0° C.

The solution produced by the preceding coupling reaction is brought to a pH level of 1.0 with concentrated HCl at 0° C., and 500 milliliters of ice cold water is added. The resulting product is filtered and the residue washed with water (3 aliquots of 100 ml). The crude residue product is mixed with 2.5 grams of $KHCO_3$ and 250 milliliters of water, and a stirred cell separation is conducted using an F-type membrane (Spectrum Ultra-por, Type F MWCO:50,000—Spectra Medical Industries, Los Angeles, Calif.) under nitrogen gas. The ultrafiltration is continued until the filtrate is colorless, as indicated by nonabsorption of light having a wavelength of 570 nanometers. The reddish-brown pure product obtained after the filtrate is dried in a desiccator is referred to as PR/APE/MMA/MAPTAC (PAMM).

Next, sufficient PAMM is added to a 10% solution of MMA/MAPTAC solvent (acid form) in N,N-dimethylacetamide (DMAC) to produce a solution with 15% PAMM by weight. (This solution, which is used to overcoat pH pellet 25 and thus comprises pH indicator matrix material 26, is referred to as "DEF-1.") A 5% solution of polyethylene oxide (PEO) in DMAC is added in sufficient quantity to part of this solution to produce a solution that includes 1–3% PEO solids by weight, producing a second solution, which is used to form pH sensitive analyte material 26 and which is referred to as "DEF-1 with PEO").

The preparation of gold foil for making pH sensitive film from which pH pellets 25 are punched is generally identical to that described above in respect to making $CO_2$ pellets 21 and 41. A 1.25 centimeter square of the gold foil is flattened onto a clean glass slide and adhesive tape is used to anchor two opposite sides of the foil to the slide. The gold foil is secured such that the surface of the foil is flat and the distance between the two pieces of tape is 1 centimeter. Excess adhesive tape is removed with a razor blade by cutting along the edges of the foil that are not taped. Next, adhesive tape is placed over the other two sides of the foil, such that the total exposed area of the gold foil is 1 square centimeter; the final two pieces of tape extend over the first two pieces of tape (which were trimmed off right at the foil edge). Bull-nosed tweezers are used to press the edges of adhesive tape down on the gold foil. Any air pockets between the pieces of adhesive tape and the glass slide and foil are removed.

To form the borders around the foil-backed area that will receive the dye, a bead of NOA-81 adhesive is placed along the tape on two sides of the gold foil. By using a No. 2 paint brush, the adhesive is brought over the tape and right up to the surface of the foil. The adhesive is allowed to cure for about 5 minutes. It can be appreciated that after the application of the adhesive onto the taped surfaces on all four sides of the gold foil, a recess is formed on top of the gold foil such that when the polymer matrix solution is applied to the gold foil, the polymer matrix solution tends to stay within the borders of the gold foil.

Next, 135 microliters of "DEF-1 with 1-3% PEO" in solution is applied over the gold surface with a digital micropipette. The entire gold foil mount is placed on a hot plate set to a temperature of from 45°-55° C. and dried with a drying tube for about two hours. The resulting pH sensitive film is cut from the glass slide, mounted for punching, and punched immediately. The mounting and punching protocol is identical to that for forming the $CO_2$ pellets, as discussed above. After the pH pellets are punched, they may be used in the production of the sensor comprising the present invention.

Lastly, an $O_2$ indicator matrix 27 (27') and 47 (47') solution is prepared for sensing oxygen. However, the polymer matrix used as a carrier for the $O_2$ sensitive indicator molecules is unlike the polymer matrix used for both the $CO_2$ and pH pellets. Preferably, a hydrophobic silicone material such as SC-35 (Hold America) is used for the polymer matrix, and a suitable oxygen analyte indicator molecule such as a porphyrin compound is mixed into the polymer matrix to produce a solution suitable for forming the $O_2$ indicator matrix. The relatively high molecular weight porphyrin is insoluble in aqueous solution and so need not be covalently bonded to the polymer matrix. The specific phosphorescent indicator molecule is preferably selected from among platinum or palladium derivatives of tetrafluorophenylporphyrin, tetraphenylporphyrin, tetrabenzporphyrin, tetrafluorobenzporphyrin, and tetrachlorobenzporphyrin. Particularly preferred are photostable, fluorinated derivatives of such metalloporphyrins. In the physiological pressure range of 0-150 torr, platinum tetraphenylporphyrin provides a lifetime curve that is especially suitable for determining $O_2$ concentration.

A typical protocol for the mixture of a porphyrin indicator molecule into the $O_2$ carrier polymer matrix is as follows. First, 0.25 grams of SC-35 silicon and 0.012 grams PtTFPP (Porphyrin Products, Logan, Utah) are weighed and mixed together. Next, 2.36 grams of tetrahydrofuran are added to the above constituents. This process results in a 10 percent solution of an oxygen indicator referred to as "PT55". When solidified, the PT55 is identified in the drawings illustrating the various embodiments of the sensor as $O_2$ indicator matrix 27 (27') and 47 (47').

Assembly and Formation of Sensor

A preferred method for assembly and formation of the first preferred embodiment, sensor 11 shown in FIGS. 1 and 2, will now be described. Each of the three optical fibers 15, 17, and 19 are carefully splayed apart and overcoated with 5 micrometers of a suitable protective polymer such as polymethylmethacrylate (PMMA). The pH pellet 25 is adherently attached to the distal end of pH optical fiber 17 and is overcoated with DEF-1 solution to form pH indicator matrix material 26, producing a hydrodynamic shape with a diameter of about 160-170 micrometers. $O_2$ optical fiber 15 is overcoated with 10 micrometers of the polymer MAPTAC. $CO_2$ pellet 21 is adherently attached to $CO_2$ optical fiber 19, but is not overcoated. The fibers are then aligned in a triangular array, with $O_2$ optical fiber 15 and $CO_2$ optical fiber 19 recessed from the distal end of pH optical fiber 17 by substantially the same distance.

A capillary tube containing $O_2$ indicator matrix 27 in solution, i.e., PT55, is used to completely encapsulate the three optical fibers, forming a bullet or hydrodynamic shape. Next, another capillary tube containing a solvent, such as toluene, is used to dissolve the PT55 from the distal end of pH optical fiber 17, exposing approximately the distal-most 10-50 micrometers of the pH optical fiber. It should be noted that the removal of the PT55 from the pH optical fiber should be accomplished such that the remaining PT55 encasing the $O_2$ and $CO_2$ optical fibers substantially retains its bullet shape. Polyimide sheath 13 is positioned such that substantially the entire length of all of the optical fibers is enclosed by polyimide sheath 13, except for the last few hundred micrometers at the distal ends of the optical fibers. Lastly, epoxy is flowed into the open end of polyimide sheath 13 (or injected through orifice 32) to form epoxy seal 30 external to the base of the bullet-shaped sheath of $O_2$ indicator matrix 27.

The assembly and construction of the other two configurations or embodiments of the invention, i.e., sensors 11' and 31 are only slightly different than the preceding disclosed method. For example, on sensor 11', polyimide sleeve 50 is installed before the three optical fibers are overcoated with PT55 to form $O_2$ indicator matrix 27'. Epoxy (not shown) is then added to seal the distal end of polyimide sheath 13' and secure the three optical fibers together before they are overcoated with PT55.

With reference to FIGS. 5 and 6, sensor 31 is made by a similar method to that discussed above in respect to sensor 11; however, in sensor 31, pH optical fiber 37 is not overcoated with $O_2$ indicator matrix 27'. Instead, $CO_2$ optical fiber 39 and $O_2$ optical fiber 35 are aligned in parallel and overcoated with PT55; however, pH optical fiber 37 with pH pellet 45 attached is overcoated with DEF-1 solution to form a hydrophilic coating 40. Coating 40 is applied to pH optical fiber 37 while it is kept splayed apart from the other two optical fibers. When the PT55 comprising $O_2$ indicator matrix 27' is dry, the pH optical fiber is aligned in parallel with the other two optical fibers. Polyimide sheath 33 is then shifted into position a few hundred micrometers behind the distal ends of the $O_2$ and $CO_2$ optical fibers and an epoxy seal 48 is applied around the distal end of polyimide sheath 33 to seal the sheath and bond the optical fibers in place.

Integration of Sensor into Blood Monitoring System

The sensor described above in respect to several preferred embodiments is usable in a blood analyte monitoring system. As an exemplary illustration, sensor 11 is integrated into a complete optical physiological blood gas concentration sensing system 52 shown in FIG. 7. The other sensors 11' and 31 are usable in such a system in an equivalent manner. System 52 comprises two light emitting diode (LED) light sources 51 and 51' that produce light having a wavelength of about 570 nanometers, two LED light sources 53 and 53' that produce light having a wavelength of about 810 nanometers, and a third LED light source 55 producing light having a wavelength of about 555 nanometers. LED's 51 and 53 are used to determine $CO_2$ concentration; LED's 51' and 53' are used to determine pH, and LED 55 is used to determine $O_2$ concentration.

In the preferred configuration of system 52, LEDs 51 and 53 in succession each generate a short pulse of light that propagates into a transmitting coupler 57, where each of the light signals is split into two branches, the signal in one branch passing into a reference detector 59 and the signal in the other branch continuing towards a reflectance coupler 61. The reference detector branch produces reference electrical signals in response to the amplitude of the light signals reaching it that are used to compensate for variations in the output of LEDs 51 and 53. The 570 nanometer wavelength light signal that passes through transmitting coupler 57 to reflectance coupler 61 is transmitted to the distal end of $CO_2$ optical fiber 19, where the light pulse is partially absorbed by $CO_2$ analyte sensitive matrix material 22 in $CO_2$ pellet 21 to a degree that depends on the concentration of $CO_2$ around the $CO_2$ pellet. The resulting attenuated light signal is reflected by reflective material 20 and propagated back as a return reflected light signal into $CO_2$ optical fiber 19. The absorption of light at the wavelength of 810 nanometers in $CO_2$ pellet 21 is negligible and not affected by $CO_2$ concentration, but is also reflected back into $CO_2$ optical fiber 19. The return reflected signals at both 570 nanometers and 810 nanometers wavelength pass into reflectance coupler 61, which diverts the return reflected signals into a reflected signal detector 65. Reflected signal detector 65 compares the amplitude of the return reflected signal at 570 nanometers wavelength to the amplitude of the return reflected signal at 810 nanometers wavelength to measure the relative absorption by $CO_2$ analyte sensitive matrix material 22. By comparing the amplitude of the return reflected signals at each wavelength to that of the signals initially generated (i.e., the electrical reference signals from reference detector 59), a measure of the $CO_2$ gas concentration at $CO_2$ pellet 21 is determined.

The operation of the pH sensing portion of system 52 is very similar to the above-described $CO_2$ sensing portion. Following the initial light pulse from LED 51', LED 53' also produces a light pulse which is transmitted into a transmitting coupler 57'. Both light signals are split between a reference branch and a detection branch by transmitting coupler 57'. The signals which pass on toward the reflectance coupler are transmitted to the distal end of pH optical fiber 17 where the light pulse at 570 nanometers wavelength is absorbed by pH pellet 25 as a function of hydrogen ion concentration in the fluid around the pH pellet. The attenuated light signal at 570 nanometers wavelength is reflected by the layer of reflective material 24 in pH pellet back into pH optical fiber 17. The absorption of light at 810 nanometers wavelength in pH pellet 25 is negligible and is not affected by the hydrogen ion concentration (pH) of the fluid around it. Return reflected signals at both 570 and 810 nanometer wavelengths are conveyed by pH optical fiber 17 into a reflectance coupler 61', which diverts the return reflected signals into a reflected signal detector 65'. By comparing the return reflected signals at each wavelength and the amplitude of the light signal initially generated (i.e., the reference electrical signal determined in a reference detector 59'), a measure of the pH around the sensor is determined.

The operation of the $O_2$ sensing portion of system 52 is somewhat different than the other portions. The light pulse produced by LED 55 travels through a coupler 67, and into $O_2$ optical fiber 15. At the distal end of $O_2$ optical fiber 15, the light pulse excites $O_2$ analyte indicator matrix 27 (PT55) to phosphoresce. The resulting phosphorescent light signal is conveyed by $O_2$ optical fiber 15 back to coupler 67. From coupler 67, this signal is diverted through an optical passband filter 69. The filtered phosphorescent light signal is monitored by a detector 71. By measuring the phosphorescence decay time of this light signal, the oxygen gas concentration at sensor 11 is determined. The higher the concentration of $O_2$ to which sensor 11 is exposed, the faster the phosphorescence is quenched.

It will be appreciated that although several preferred embodiments of the present invention have been described above, further changes can be made therein, as will be apparent to those of ordinary skill in the art. Such variations in the invention are nevertheless within the scope of the invention as defined by the claims appended hereto.

The embodiments of the invention in which an exclusive property or privilege is claimed are defined as follows:

1. A multi-analyte sensor comprising:
  (a) a first, a second, and a third optical fiber, each optical fiber having a longitudinal axis and a distal end, the longitudinal axis corresponding to the direction that a light signal propagates through said optical fibers, all of said optical fibers being arranged in a sheath such that their longitudinal axes are substantially parallel, said sheath terminating short of the distal ends of the optical fibers, leaving an exposed portion of each optical fiber extending beyond the sheath, only two of the optical fibers being bonded together up to and around their distal ends, the distal ends of the optical fibers forming a mutually supporting array;
  (b) a first indicator matrix containing a first indicator molecule, disposed adjacent to said first optical fiber, said first indicator molecule exhibiting a first signal in response to light at a first wavelength to an extent that depends upon a first analyte concentration around the sensor;
  (c) a second indicator matrix containing a second indicator molecule, disposed adjacent to said second optical fiber, said second indicator molecule exhibiting a second signal in response to light at a second wavelength to an extent that depends upon a second analyte concentration around the sensor; and
  (d) a third indicator matrix containing a third indicator molecule, disposed adjacent said third optical fiber, said third indicator molecule exhibiting a third signal in response to light of a third wavelength to an extent that depends upon a third analyte concentration around the sensor, wherein said mutually supporting array minimizes breakage of any of the optical fibers and indicator matrices due to handling.

2. The multi-analyte sensor of claim 1, further comprising a first light reflectance material disposed adjacent said first indicator matrix and a second light reflectance material disposed adjacent said second indicator matrix, wherein said first and second signals are reflected from said first and second light reflectance materials and are indicative of the absorbance of light at said first and said second wavelengths as a function of the first and second analyte concentrations, respectively, and wherein said third signal is the phosphorescence of said third indicator molecule in response to light at said third wavelength, which varies as a function of the third analyte concentration.

3. The multi-analyte sensor of claim 1, wherein said optical fibers are aligned in a triangular array adjacent their distal ends.

4. The multi-analyte sensor of claim 1, wherein at least one of the first, second, and third indicator matrices absorbs light as a function of one of the first, second, and third analyte concentrations, and at least another of said indicator matrices emits light when excited, said light emission continuing for a time interval that is a function of another of said analyte concentrations.

5. The multi-analyte sensor of claim 1, wherein at least one indicator matrix is substantially pellet shaped and is attached to a substantially planar face of the distal end of a corresponding one of the optical fibers.

6. The multi-analyte sensor of claim 1, wherein the distal ends of said first, second, and third optical fibers are overcoated such that said multi-analyte sensor has a hydrodynamic shape.

7. The multi-analyte sensor of claim 1, wherein two of said optical fibers each extend distally beyond the other of the optical fibers.

8. The multi-analyte sensor of claim 1, wherein said first indicator matrix and said second indicator matrix are substantially pellet shaped, and are attached to a planar face at the distal end of said first optical fiber and said second optical fiber, respectively.

9. The multi-analyte sensor of claim 1, wherein the distal ends of at least two of said optical fibers are overcoated with a hydrophobic material.

10. The multi-analyte sensor of claim 1, wherein the distal end of at lest one of the optical fibers is overcoated with a hydrophilic material.

11. The multi-analyte sensor of claim 1, wherein said first indicator matrix and said second indicator matrix each comprise substantially cylindrically shaped pellets, and said pellets are attached to transverse planar surfaces formed on the distal end of said first optical fiber and said second optical fiber, respectively, each pellet including a light reflective layer disposed opposite the transverse planar surface of the optical fiber to which the pellet is attached, each said light reflective layers on the pellets reflecting light exiting the transverse planar surface of the respective first and second optical fibers back into said optical fibers.

12. The multi-analyte sensor of claim 11, wherein the distal ends of said first, second, and third optical fibers are overcoated such that said multi-analyte sensor has a hydrodynamic shape.

13. The multi-analyte sensor of claim 11, wherein the distal end of one of the optical fibers is not overcoated and the distal ends of the other two optical fibers are overcoated with at least one of the indicator matrices in order to bond the two optical fibers together.

14. A medical sensor for a plurality of analytes comprising: a plurality of optical fibers having distal ends extending longitudinally in parallel alignment, said optical fibers being enclosed in a common protective sheath over at least part of their length, but exposed at their distal ends, only two of said optical fibers being configured and bonded together by a matrix material that encompasses their distal ends; a plurality of different analyte indicator materials, each analyte indicator material sensitive to the concentration of one of the plurality of analytes, each analyte indicator material being disposed generally at the distal ends of the optical fibers so as to vary a light signal propagated through the optical fibers as a function of the concentration of a different one of the analytes, at least one of the analyte indicators comprising the matrix material used to bond the two optical fibers together; wherein the optical fibers form a mutually supportive array that resists breakage of any one of the optical fibers comprising the array.

15. A method for manufacturing a blood gas sensor comprising the steps of:
  (a) aligning a first, a second, and a third optical fiber within a sheath such that the longitudinal axes of all said optical fibers are substantially parallel, all of the optical fibers having distal ends that extend beyond where the sheath terminates so that the distal ends are exposed;
  (b) applying a first indicator matrix containing a first indicator molecule adjacent to the distal end of said first optical fiber, said first indicator molecule exhibiting a first signal in response to light at a first wavelength to an extent dependent upon a first analyte concentration around the sensor;
  (c) applying a second indicator matrix containing a second indicator molecule adjacent to the distal end of said second optical fiber, said second indicator molecule exhibiting a second signal in response to light at a second wavelength to an extent dependent upon a second analyte concentration around the sensor; and
  (d) applying a third indicator matrix material containing a third indicator molecule up to and around said distal ends of only two of said optical fibers thereby bonding the exposed portion of the two optical fibers together, said third indicator molecule exhibiting a third signal in response to light of a third wavelength to an extent which depends upon a third analyte concentration around the sensor, the two optical fibers bonded together providing a mutually supportive array, so that all of said optical fibers mutually reinforce each other and are resistant to breakage.

16. The method of claim 15, wherein the step of aligning all of said optical fibers comprises the step of aligning said optical fibers in a triangular array.

17. The method of claim 15, wherein the step of aligning comprises the step of positioning the distal ends of the optical fibers so that they are not all transversely aligned.

18. The method of claim 16, wherein prior to the alignment of said optical fibers, all of said optical fibers are overcoated with a thin coat of a protective polymer.

19. The method of claim 16, further comprising the step of overcoating at least two of said optical fibers with a hydrophobic material.

20. The method of claim 16, wherein the step of applying one of said first and said second indicator matrices comprises the step of affixing a pellet to one of said first and said second optical fibers.

21. The method of claim 20, wherein said pellet comprises a light reflectance material.

22. The method as claimed in claim 16, further comprising the step of overcoating the distal ends of the optical fibers to form a hydrodynamic shape.

* * * * *